United States Patent [19]

Sulzbach et al.

[11] B 4,013,661

[45] Mar. 22, 1977

[54] SUBSTITUTED 1,2-DIHYDROPYRIDINES AND PROCESS FOR PREPARING SAME

[75] Inventors: Reinhard A. Sulzbach, Burghausen, Germany; Abul F. M. Iqbal, Glattbrugg, Switzerland

[73] Assignee: Monsanto Company, St. Louis, Mo.

[22] Filed: Apr. 17, 1974

[21] Appl. No.: 461,685

[44] Published under the second Trial Voluntary Protest Program on March 30, 1976 as document No. B 461,685.

Related U.S. Application Data

[63] Continuation-in-part of Ser. No. 153,062, June 11, 1971, Pat. No. 3,816,439.

[30] Foreign Application Priority Data

June 19, 1970 Switzerland .................. 9393/70

[52] U.S. Cl. .................. 260/283 CN; 260/290 S; 260/290 HL; 260/294.9; 260/295 R; 260/283 SC

[51] Int. Cl.² .............. C07D 215/58; C07D 211/92

[58] Field of Search ..... 260/290 S, 290 HL, 295 R, 260/294.9, 283 CN, 283 SC

[56] References Cited

UNITED STATES PATENTS 3,816,439   6/1974   Sulzbach et al. .............. 260/295 R

OTHER PUBLICATIONS

Shostrakovskii et al., Chem. Abstr., vol. 59, 11550e–11550h, Nov. 1963.

*Primary Examiner*—R. Gallagher
*Assistant Examiner*—Mary C. Vaughn

[57] ABSTRACT

Substituted 1,2-dihydropyridines of the formula

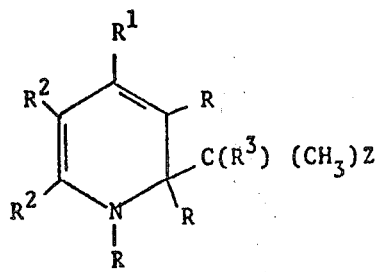

in which R and $R^2$ are selected from the group consisting of hydrogen, $-NH_2$, silyl, silyl linked via oxygen, silyl linked via nitrogen, sulfamyl, organosulfonamido, nitro, organic radical, organic radical linked via oxygen, organic radical linked via sulfur, organic radical linked via nitrogen, organic radical linked via $-SO-$ and organic radical linked via $-SO_2-$; with the proviso that the $R^2$ groupings when joined together form an ortho condensed cyclic or polycyclic hydrocarbon; $R^1$ is a member selected from the group consisting of hydrogen, $-NH_2$, silyl, silyl linked via oxygen, silyl linked via nitrogen, sulfamyl, organosulfonamido, nitro, organic radical, organic radical linked via oxygen, organic radical linked via sulfur, organic radical linked via nitrogen, organic radical linked via $-SO-$ organic radical linked via $-SO_2-$, mercapto, sulfino and sulfo; $R^3$ is a member selected from the group consisting of hydrogen, halogen, and methyl; and Z is a member selected from the group consisting of halogen and an electron-withdrawing group containing an electronegative atom doubly or triply bonded to a more positive atom which atom is singly bonded to the carbon atom attached to the pyridine ring. Exemplary of such compositions is 1,4-bis(trimethylsilyl)-2-(1-cyanoethyl)-1,2-dihydropyridine. The compounds of the invention are useful as antioxidants for polyphenyl ethers, as stabilizers for halogenated polyhydrocarbons, as curing agents for silicones and epoxide resins, as dyeing improvers for polyesters and as fuel additives for imparting hypergolic properties.

5 Claims, No Drawings

SUBSTITUTED 1,2-DIHYDROPYRIDINES AND PROCESS FOR PREPARING SAME

The present patent application is a continuation-in-part of Ser. No. 153,062, filed June 11, 1971 now U.S. Pat. No. 3,816,439.

BACKGROUND OF THE INVENTION

1. Field of the Invention:

This invention relates to substituted 1,2-dihydropyridines of the formula (I) 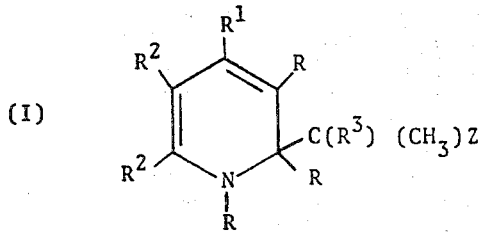

in which R and $R^2$ are selected from the group consisting of hydrogen, $-NH_2$, silyl, silyl linked via oxygen, silyl linked via nitrogen, sulfamyl, organosulfonamido, nitro, organic radical, organic radical linked via oxygen, organic radical linked via sulfur, organic radical linked via nitrogen, organic radical linked via $-SO-$ and organic radical linked via $-SO_2-$; with the proviso that $R^2$ groupings when joined together form an ortho condensed cyclic or polycyclic hydrocarbon; $R^1$ is a member selected from the group consisting of hydrogen, $-NH_2$, silyl, silyl linked via oxygen, silyl linked via nitrogen, sulfamyl, organosulfonamido, nitro, organic radical, organic radical linked via oxygen, organic radical linked via sulfur, organic radical linked via nitrogen, organic radical linked via $-SO-$, organic radical linked via $-SO_2-$, mercapto, sulfino and sulfo; $R^3$ is a member selected from the group consisting of hydrogen, halogen and methyl; and Z is a member selected from the group consisting of halogen and an electron-withdrawing group containing an electronegative atom doubly or triply bonded to a more positive atom, which atom is singly bonded to the carbon atom attached to the pyridine ring. A further aspect of this invention relates to a process for preparing substituted 1,2-dihydropyridines of formula (I) by reacting a 1,4-dihydropyridine of the formula (II) 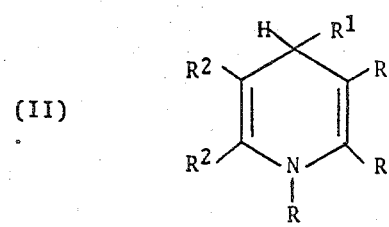

wherein R, $R^1$ and $R^2$ have the same significance as above with a vinyl compound of the formula (III) 

wherein $R^3$ and Z have the same significance as above, at a temperature of from about 20°C to about 100°C under anhydrous and nonoxidizing conditions.

DESCRIPTION OF THE PRIOR ART

The addition of vinyl compounds having an activated double bond to dihydropyridines has not been previously accomplished. The reaction of 1-trimethyl silyl-1,4-dihydropyridine with ethylacrylate as reported by E. J. Moriconi et al. in Journal Organic Chemistry 34, 3672 1969 led to no isolatable product. The 1,4-dihydropyridine contains the elements of cross-conjugated enamines. Hence, the product of (IV) or (V) would normally be expected on reacting, e.g., acrylonitrile (Fleming et al., Journal Chemical Society 2165, 1964).

(IV) 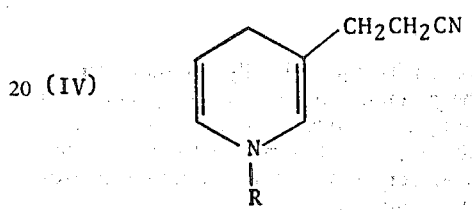

(V) 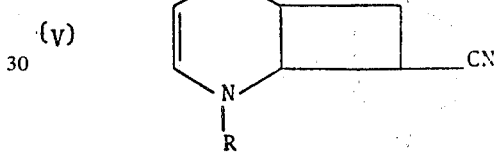

SUMMARY OF THE INVENTION

It is an object of the present invention to provide substituted 1,2-dihydropyridines of the formula (I) 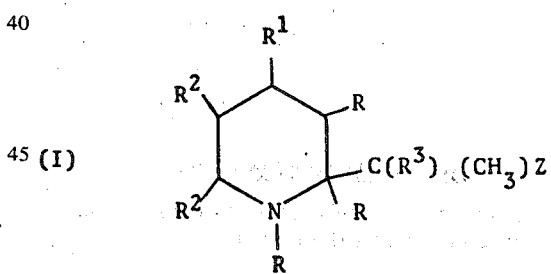

It is a further object of the present invention to provide a convenient process for producing the substituted 1,2-dihydropyridines.

Other objects and advantages of the present invention will be apparent from the specification and appended claims.

It has been found in accordance with the present invention that the reaction of 1,4-dihydropyridines of the formula (II) 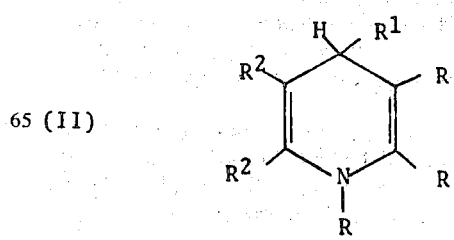

with vinyl compounds of the formula (III) 

surprisingly leads to the substituted 1,2-dihydropyridines of the formula

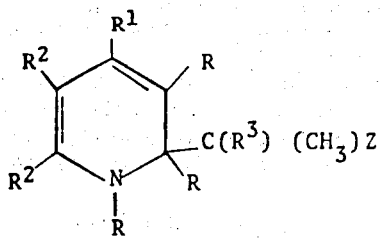

In the reaction addition surprisingly occurs on the 2-position of the pyridine nucleus and the product still contains two ethylenic bonds which are, however, conjugated. With, e.g., 1-4-bis(trimethylsilyl)-1,4-dihydropyridine and acrylonitrile the addition proceeds according to the equation (VI) 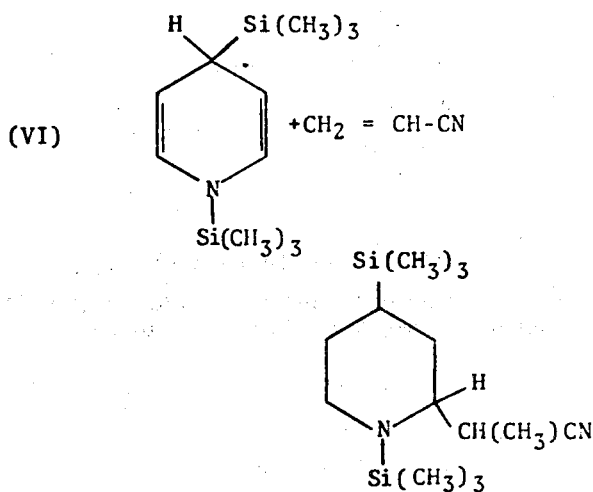

DETAILED DESCRIPTION

The 1,4-dihydropyridines useful in the process of the present invention are of the formula (II) 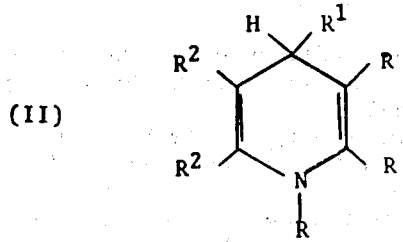

It is essential that the 1,4-dihydropyridines have at least one hydrogen atom on the 4-position of the pyridine ring. Since the reaction of the present invention affords substitution on the 2-position of the pyridine ring, no substituent being larger than tertiary butyl should be on that place.

Methods for preparing the 1,4-dihydropyridines are well known to the art. The addition of certain reagents to pyridine, such as for example, lithium phenyl, yields upon careful hydrolysis the corresponding 1,4-dihydropyridines, showing a substituent at least on the 4-position, e.g., 4-phenyl-1,4-dihydropyridine.

Another method for preparing the 1,4-dihydropyridines comprises the reduction of pyridinium salts with sodium hydrosulfite. The resulting compounds possess at least a substituent on the ring nitrogen atom. Numerous pyridines can be converted to the pyridinium salts and further to the corresponding 1,4-dihydropyridines and many starting compounds are available.

A recently discovered method for the preparation of the 1,4-dihydropyridines comprises the reaction of pyridine or a pyridine derivative with a halosilane, e.g., trimethylchlorosilane, in the presence of alkali metal and an inert polar solvent. This procedure permits the preparation of 1,4-disilylated 1,4-dihydropyridines, e.g., 1,4-bis-(trimethylsilyl)-1,4-dihydropyridine, which are useful starting compounds for carrying out the present invention.

Suitable 1,4-dihydropyridines may also be obtained by the so-called Hantzsch synthesis and modifications thereof such as the condensation of $\alpha,\beta$-unsaturated aldehydes and ketones with methylenic ketimines, the condensation of oxo compounds with ammonia or amines, the reaction of an aldehyde and a ketone with a ketimine, the reaction of ketones with ketimines, etc. Such compounds are described in detail in the text THE CHEMISTRY OF HETEROCYCLIC COMPOUNDS, Pyridines and its Derivatives, Part I (1960, Interscience Publishers, Inc., New York) and are compiled in Tables I–6, II-107, II-122, II-123 and II-125.

On contemplating the occurring substituents it is apparent that the term "organic radical" as used herein is to be taken in the broad sense and includes, for example, carboxyl (—COOH), carbamyl (—CONH₂), ureido (—NHCONH₂), guanyl

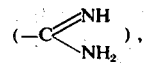

cyano (—CN), cyanato (—OCN) as well as other simple carboncontaining groups. The organic radicals attached via an oxygen, sulfur or nitrogen atom generally will be hydrocarbyl groups. In the latter case the substituent typically will be a secondary or primary amino group and, of course, heterocyclic amino groups such as pyrrolidino, piperidino and morpholino.

The organic groups attached via SO and SO₂ to the pyridine ring in general will also be hydrocarbyl groups. These are known as organosulfinyl and organosulfonyl groups such as benzenesulfonyl, toluenesulfinyl and sulfanilyl (p-H₂NC₆H₄SO₂-) groups.

The term "silyl" as used herein is understood to include groups having Si-Si or Si-O-Si skeleton, such as pentamethyldisilanyl and pentamethyldisiloxanyl groups. Generally, the silyl groups will be trihydrocarbylsilyl groups such as trimethylsilyl and triphenylsilyl. Because of full equivalency, the cyclic silyl groups such as 1-methylsilacyclopentyl and 1-phenylsilacyclohexyl, however, will also be included.

The term "sulfamyl" as used herein indicates a group of the formula —SO₂NH₂, including organic derivatives thereof, such as sulfamyl groups having a secondary or tertiary amino group such as phenylsulfamyl and dimethylsulfamyl groups.

The term "organosulfonamido" as used herein signifies a substituent of the formula —NH—SO₂R wherein R is an organic group. Illustrative examples are toluenesulfonamido, methanesulfonamido, dodecanesulfonamido and sulfanilamido (p-$H_2NC_6H_4SO_2NH$-).

Under the prefixes sulfino and sulfo are comprised the groups having the formula —$SO_2H$ or —$SO_3H$, whilst "mercapto" is the —SH group.

As an example of a starting compound wherein the $R^2$ groups are linked together once to form an ortho-condensed cyclic system is 1,4-dihydroquinoline, whereas 1,4-dihydro-6,7-benzoquinoline is representative of an ortho-condensed polycyclic system. In general, the cyclic system which is ortho-condensed with the pyridine ring will be aromatic or hydroaromatic and typically possesses 5 to 20 carbon atoms.

In order to still better recognize the suitable starting materials, especially the sylylated 1,4-dihydropyridines, reference is directed to Applicants' copending United States patent application having attorney's docket number C-07-21-0137.

To the skilled worker it will be apparent that the kind of substituents as well as their distribution on the pyridine nucleus will depend on the method of preparation. On considering the formula (II) together with the teachings supplied above, it will be necessary to select the appropriate starting compounds for practicing the invention. It is also clear that a substituent $R^1$ and $R^2$ may be 1,4-dihydropyridyl group such as, for example, in the compound N,N-diacetyl-1,4,1', 4'-tetrahydro-4,4'-dipyridyl, which is twice able to undergo the reaction of the invention.

The formula (III) of the vinyl compounds serving as second reactant in the process of the present invention has been set forth herein. Examples of such vinyl compounds are acrylic acid, methacrylic acid, vinyl sulfonic acid, vinyl phosphonic acids, vinyl phosphinic acids and derivatives thereof such as esters, e.g., methyl, dodecyl, cyclohexyl and phenyl ester; amides, e.g., diethylamide, dioctylamide, stearylamide, anilide, pyrrolidide and morpholidide and halides, e.g., fluoride, chloride bromide and iodide; acrylic and methacrylic acid anhydride; acrylonitrile, methacrylonitrile, etc., and the like. Additional examples of suitable starting compounds are vinyl ketones, e.g., vinyl methyl ketone, vinyl allyl ketone, divinyl ketone and vinyl phenyl ketone, and the corresponding thioketones; acrolein, methacrolein, sulfones, e.g., vinyl propyl sulfone, divinyl sulfone and vinyl phenyl sulfone, and the corresponding sulfoxides having SO instead of $SO_2$ linkage; nitro ethylene, 3-nitro propene; vinyl esters of carboxylic acids, e.g., vinyl acetate, vinyl caproate, vinyl benzoate and divinyl phthalate; tertiary vinyl phosphine oxides, divinyl phosphine oxides and trivinyl phosphine oxide; vinyl halides such as vinyl chloride, vinyl bromide, vinyl fluoride, vinylidene chloride and vinylidene fluoride; and butadiene isoprene, and styrenes.

In carrying out the reaction of the present invention, reactants (II) and (III) are mixed typically and preferably in equimolar amounts. It is clear in some instances, depending on the amount of 1,4-dihydropyridine moieties present in the starting material, the amount of the vinyl compound is preferably correspondingly increased. Care should be taken to avoid any contact of the reaction mixture with oxygen (air) or moisture. Therefore, the reaction is preferably conducted in an inert atmosphere such as, for example, nitrogen or argon. The addition of highly activated vinyl compounds to the 1,4-dihydropyridines occurs at approximately room temperature (about 20°C). With less reactive vinyl compounds temperatures up to about 100°C are preferred. In order to hinder comparative polymerization of the vinylic reactant, it is preferred to add said reactant gradually to the 1,4-dihydropyridine with stirring. When the reactants as well as the end product are in the liquid state, the reaction can be carried out without a solvent. However, an inert solvent such as tetrahydrofuran is preferably employed since it permits ease of handling and generally allows better control of the reaction.

The 1,4-dihydropyridines bearing an acid group such as carboxyl, sulfo and sulfino are preferably brought to reaction in the form of a salt, e.g., alkali or tertiary amine salt.

The end products may be isolated by any suitable procedure such as, for example, by fractional distillation, crystallization, chromatography and the like.

The substituted 1,2-dihydropyridine compounds of the present invention are useful as catalysts for the addition of chlorosilane, e.g., trichlorohydrosilane to $\alpha,\beta$-unsaturated compounds such as have been enumerated above for vinylic reactants (III). They are further useful as co-catalysts in conjunction with Ziegler catalysts for the polymerization of $\alpha$-olefins, e.g., ethylene and propylene. Also valuable antioxidants for, e.g., polyphenylethers; stabilizers for halogenated polyhydrocarbons, e.g., polyvinylchloride and chloroprene; curing agents for silicones and epoxide resins; dyeing improvers for polyester; U.V. light absorbants and corrosion inhibitors. They can further serve in the production of photoconductive layers of electrophtoographic materials.

Methods for employing the compounds of the present invention in the above uses will be readily apparent to the skilled worker.

When the compounds of the present invention bear a hydrogen atom in the 2-position of the pyridine ring, they are comparatively strong reductants due to their great tendency to restore to the full aromatic system. If, for example, 1-methyl-2-(1-carbethoxyethyl)-1,2-dihydropyridine is brought into contact with combustible materials such as paper, wood, textiles and the like in the presence of oxygen (air), oxidation takes place rapidly with generation of heat to complete carbonization under evolution of smoke; whereby spontaneous ignition may arise. Therefore, such compounds are useful as additives to fuels and may impart hypergolic properties or they can be used as ignitors for rocket motors in admixture of other suitable agents, e.g., allyl catechol.

The compounds of the present invention having a hydrogen atom in the 2-position are also valuable as reducing agents for preparing hydrogenation catalysts from rhodium, iridium or platinum compounds.

It will become apparent to the skilled worker from formula (I) that the compounds of the present invention are versatile intermediates. When such compounds contain a hydrogen atom in the 2-position and either no substituent on the ring nitrogen atom or a substituent, e.g., trimethylsilyl, which is oxidatively cleavable, they can be converted to the wholly aromatic pyridines by contacting the oxygen (air). Otherwise, the N-substituted 1,2-dihydropyridines can be converted to the corresponding pyridinium salts.

Reduction of the compounds of the present invention to the corresponding piperidine derivatives is effected by catalytic hydrogenation, e.g., low pressure hydrogenation in the known manner. With 1,2-dihydropyridines, selective reduction of the dihydropyridine nucleus can be achieved and hence other reducible groups such as nitrilo, carbalkoxy and carbophenoxy groups will be preserved. This is not the case in the reduction of corresponding aromatic pyridines.

As is seen, the compounds of the present invention possess conjugated double bonds which will allow various Diels-Alder reactions with appropriate dienophilic compounds. For example, a further molecule of the vinylic reactant (III) can be added to the pyridine ring by the same procedure. However, somewhat more drastic conditions will be needed such as heating at, e.g., 90°C for extended periods.

The invention will be understood more fully by reference to the following specific examples. It is understood that the examples are presented for the purpose of illustration only and are not intended as a limitation of the invention.

This application is a continuation-in-part of Ser. No. 153,062 filed June 14, 1971.

EXAMPLE 1

To 22.6 g (0.1 mol) of 1,4-bis-(trimethylsilyl)-1,4-dihydropyridine are added by drops 5.31 g (0.1 mol) of acrylonitrile within 30 minutes in an inert atmosphere. The mixture is subsequently stirred for several hours at room temperature. Fractional distillation yields 19.9 g (72%) of 1,4-bis-(trimethylsilyl)-2-(1-cyanoethyl)-1,2-dihydropyridine; b.p. 78°C/0.003 mm; yellow oil.

EXAMPLE 3

A mixture consisting of 11.3 g (0.05 mol) of 1,4-bis-(trimethylsilyl)-1,2-dihydropyridine and 10.6 g (0.2 mol) of acrylonitrile is heated in an argon atmosphere at 90°C for 17 hours and distilled.

Yield 14.2 g (86%) of 1,4-bis-(trimethylsilyl)-2-(1-cyanoethyl)-1,2,3,6-tetrahydropyridine-3,6-endo-2-cyanoethylene or bicyclo-2,5-bis-(trimethylsilyl)-2-aza-3-(1-cyanoethyl)-8-cyano-[2,2,2]-oct-5-ene; b.p. 130°–140°C/0.01 mm.

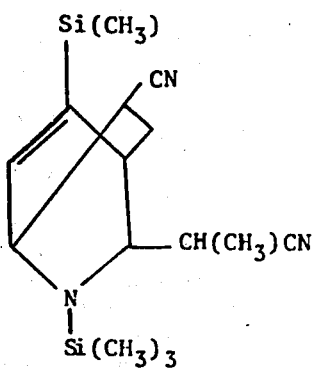

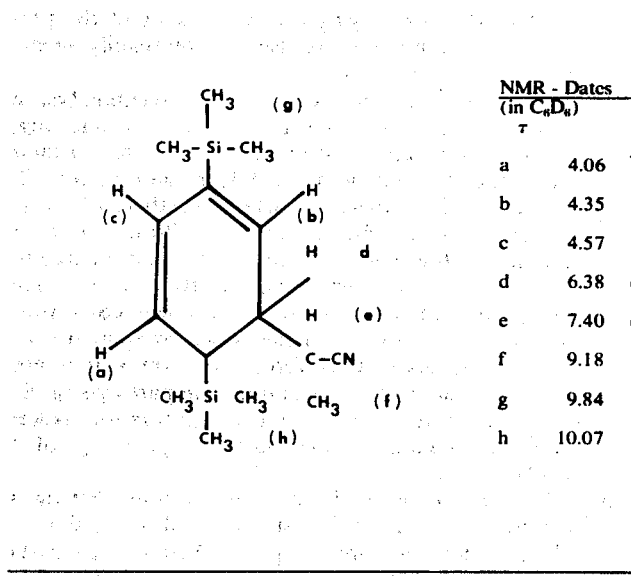

| | NMR - Dates (in $C_6D_6$) | |
|---|---|---|
| | τ | J cps |
| a | 4.06 | a-c 6.6, a-d 1.1 |
| b | 4.35 | a-b 1.1 |
| c | 4.57 | b-d 5.8, b-c 1.18 |
| d | 6.38 | d-e 8.4 |
| e | 7.40 | e-f 7.3 |
| f | 9.18 | |
| g | 9.84 | |
| h | 10.07 | |

Analysis calc'd % C 60.36 H 9.41 N 10.06 Si 20.17. found % C 60.59 H 9.03 N 10.10 Si 20.32.

EXAMPLE 2

Following the procedure of Example 1, 8.6 g (0.1 mol) of acrylic acid methyl ester are brought to reaction with 22.6 g (0.1 mol) of 1,4-bis-(trimethylsilyl)-1,4-dihydropyridine. Upon addition of 20 ml of tetrahydrofuran the mixture is stirred at 50°C for 70 hours. The distillation in high vacuum yields 21.1 g (68%) of 1,4-bis-(trimethylsilyl)-2-(1-carbomethoxyethyl)-1,2-dihydropyridine.

The product is clean white after sublimation in vacuum and possesses a melting point of 108°C.

Analysis calc'd % C 61.57 H 8.81 N 12.67 Si 16.94. found % C 62.38 H 8.90 N 13.26 Si 15.41.

The product is converted on stirring for 3 hours with wet ether to 4-trimethylsilyl-2-(1-cyanoethyl)-1,2,3,6-tetrahydropyridine-3,6-endo-2-cyanoethylene; viscous yellow oil.

Moreover, the product is converted on heating for 24 hours in alcoholic solution of KOH to the corresponding dicarboxylic acid, namely 4-trimethylsilyl-2-(1-carboxyethyl)-1,2,3,6-tetrahydropyridine-3,6-endo-2-carboxyethylene; white solid.

Since many embodiments of this invention may be made and since many changes may be made in the embodiment described the foregoing is to be interpreted as illustrative only and the invention is defined by the claims appended hereto.

EXAMPLE 4

A mixture consisting of 27.5 g (0.1 mol) of 1,4-bis-(trimethylsilyl)-1,4-dihydroquinoline and 6 g (0.1 mol) of acrylonitrile is heated in an inert atmosphere at 100°C for 150 hours. Fractional distillation yields 24.2 g (72%) of 1,4-bis-(trimethylsilyl)-2-(1-cyanoethyl)-1,2-dihydroquinoline: yellow-green oil, b.p. 106°–108°C/0.001 mm.

Analysis calc'd % C 65.79 H 8.59 N 8.52 Si 17.10 MW 328.6. found % C 65.49 H 8.76 N 8.60 Si 16.54 MW 321.0.

EXAMPLE 5

A mixture consisting of 0.3 g (0.026 mol) of 1-(2,6-dichlorobenzyl)-1,4-dihydropyridine, 1.55 g (0.29 mol) of acrylonitrile and 10 ml of n-hexane is heated in an inert atmosphere at 60°C for 48 hours. Then, the solvent and unreacted acrylonitrile are distilled off and 7.35 g of a yellow residue are obtained. Fractional sublimation in high vacuum yields 4.1 g (53%) of 1-(2,6-dichlorobenzyl)-2-(1-cyanoethyl)-1,2-dihydropyridine.

EXAMPLE 6

7 g (0.05 mol) of 1-phenyl-1,4-dihydropyridine and 2.92 g (0.055 mol) of acrylonitrile are brought to reaction according to the procedure of Example 5. Yield 6.5 g (61%) of 1-phenyl-2-(1-cyanoethyl)-1,2-dihydropyridine.

We claim:
1. Process for the production of 1,4-bis-(trimethylsilyl-2-(1-carbomethoxyethyl)-1,2-dihydropyridine which comprises reacting acrylic acid methyl ester with 1,4-bis-(trimethylsilyl)-1,4-dihydropyridine under anhydrous and nonoxidizing conditions.
2. Process for the production of 1,4-bis-(trimethylsilyl)-2-(1-cyanoethyl)-1,2,3,6-tetrahydropyridine-3,6-endo-2-cyanoethylene which comprises reacting acrylonitrile with 1,4-bis-(trimethylsilyl)-1,4-dihydropyridine under anhydrous and nonoxidizing conditions.
3. Process for the production of 1,4-bis-(trimethylsilyl)-2-(1-cyanoethyl)-1,2-dihydroquinoline which comprises reacting acrylonitrile with 1,4-bis-(trimethylsilyl)-1,4-dihydroquinoline under anhydrous and nonoxidizing conditions.
4. Process for the production of 1-(2,6-dichlorobenzyl)-2-(1-cyanoethyl)-1,2-dihydropyridine which comprises reacting acrylonitrile with 1-(2,6-dichlorobenzyl)-1,4-dihydropyridine under anhydrous and nonoxidizing conditions.
5. Process for the production of 1-phenyl-2-(1-cyanoethyl)-1,2-dihydropyridine which comprises reacting acrylonitrile with 1-phenyl-1,4-dihydropyridine under anhydrous and nonoxidizing conditions.

* * * * *